United States Patent
Sprecher et al.

(10) Patent No.: US 9,707,219 B2
(45) Date of Patent: Jul. 18, 2017

(54) LOSMAPIMOD FOR USE IN TREATING GLOMERULAR DISEASE

(71) Applicant: GlaxoSmithKline Intellectual Property (No.2) Limited, Brentford (GB)

(72) Inventors: Dennis Sprecher, Pennsylvania, PA (US); Robert Nicholas Willette, Pennsylvania, PA (US)

(73) Assignee: GlaxoSmithKline Intellectual Property (No.2) Limited, Brentford Middlesex (GB)

( * ) Notice: Subject to any disclaimer, the term of this patent is extended or adjusted under 35 U.S.C. 154(b) by 0 days.

(21) Appl. No.: 14/903,694

(22) PCT Filed: Jul. 8, 2014

(86) PCT No.: PCT/EP2014/064508
§ 371 (c)(1),
(2) Date: Jan. 8, 2016

(87) PCT Pub. No.: WO2015/004089
PCT Pub. Date: Jan. 15, 2015

(65) Prior Publication Data
US 2016/0220550 A1 Aug. 4, 2016

Related U.S. Application Data
(60) Provisional application No. 61/844,491, filed on Jul. 10, 2013.

(51) Int. Cl.
*A61K 31/44* (2006.01)
*A61K 31/455* (2006.01)
*A61K 45/06* (2006.01)

(52) U.S. Cl.
CPC ............ *A61K 31/455* (2013.01); *A61K 45/06* (2013.01)

(58) Field of Classification Search
CPC .................................................. A61K 31/455
USPC .......................................................... 514/455
See application file for complete search history.

(56) References Cited

FOREIGN PATENT DOCUMENTS

| WO | 03/068747 | | 8/2003 | | |
| WO | WO 03/068747 | * | 8/2003 | ......... | A61K 31/4418 |
| WO | 2007/144390 | | 12/2007 | | |
| WO | WO 2007/144390 | * | 12/2007 | ......... | A61K 31/4418 |
| WO | 2014/014706 | | 1/2014 | | |

OTHER PUBLICATIONS

Thomas, et al., Chronic Type IV Phosphodiesterase Inhibition Protects Glomerular Filtration Rate and Renal and Mesenteric Blood Flow in a Zymosan-Induced Model of Multiple Organ Dysfunction Syndrome Treated with Norepinephrine, Journal of Pharmacology and Experimental Therapeutics 296(1):168-174 (2001).
Stambe, et al., p38 Mitogen-Activated Protein Kinase Activation and Cell Localization in Human Glomerulonephritis: Correlation with Renal Injury, Journal of the American Society of Nephrology 15(2):326-336 (2004).
Olzinski, et al., Hypertensive target organ damage is attenuated by a p38 MAPK inhibitor: Role of systemic blood pressure and endothelial protection, Cardiovascular Research 66(1):170-178 (2005).
Coulthard, et al., p38<MAPK>: stress responses from molecular mechanisms to therapeutics, Trends in Molecular Medicine 15(8):369-379 (2009).
Willette, et al., Differential Effects of p38 Mitogen-Activated Protein Kinase and Cyclooxygenase 2 Inhibitors in a Model of Cardiovascular Disease, Journal of Pharmacology and Experimental Therapeutics 330(3):964-970 (2009).
International Search Report for priority U.S. Appl. No. PCT/EP2014/064508.

* cited by examiner

*Primary Examiner* — Nizal Chandrakumar
(74) *Attorney, Agent, or Firm* — James P. Riek; R Steve Thomas

(57) ABSTRACT

The present invention relates to a method of treating a glomerular disease with 6-(5-cyclopropylcarbamoyl-3-fluoro-2-methyl-phenyl)-N-(2,2-dimethylpropyl)-nicotinamide or a pharmaceutically acceptable salt thereof.

6 Claims, No Drawings

LOSMAPIMOD FOR USE IN TREATING GLOMERULAR DISEASE

This application is filed pursuant to 35 U.S.C. §371 as a United States National Phase Application of International Patent Application No. PCT/EP2014/064508 filed Jul. 8, 2014, which claims priority from U.S. Provisional Patent Application No. 61/844,491 filed in the United States on Jul. 10, 2013, each of which is incorporated herein by reference.

FIELD OF THE INVENTION

This invention relates to a new pharmaceutical use of a compound which is known in the art as a p38 kinase inhibitor. More specifically this invention relates to the use of a nicotinamide derivative in the treatment of one or more glomerular disease(s) or conditions exhibiting glomerular pathology.

BACKGROUND OF THE INVENTION

Many diseases affect kidney function by attacking the glomeruli, the clusters of looping blood vessels within the kidney where blood is cleaned/filtered. Glomerular diseases are those in which the glomeruli are no longer fulfilling this function. Damage to the glomeruli affects the kidney's ability to filter fluids and wastes properly. This leads to blood (hematuria) and/or protein (proteinuria) in the urine. Glomerular diseases are often associated with the signs and symptoms of nephrotic syndrome and predispose to acute renal failure, or progressive chronic kidney disease culminating in end-stage renal disease with dialysis or kidney transplantion.

Glomerular diseases include many conditions with a variety of differing causes but which can broadly categorised into two major categories namely, glomerulonephritis (inflammation of the tissue in the kidney that serve as a filter) and glomerulosclerosis (hardening or scarring of the blood vessels within the kidney).

Diabetic nephropathy, one of the leading causes of kidney failure in the USA, is a form of glomerular disease which is considered to be both a systemic disease, since diabetes itself is a systemic disease, and also a sclerotic diseases, because the specific damage done to the kidneys is associated with scarring.

Focal segmental glomerulosclerosis (FSGS) describes scarring in scattered regions of the kidney, typically limited to one part of the glomerulus and to a minority of glomeruli in the affected region. This condition may result from specific genetic mutations, systemic conditions, toxins or may develop as an idiopathic kidney disease.

Glomerular hypertension (or hypertensive renal disease) is a glomerular disease in which damage to the kidney is associated with chronic high blood pressure.

Current treatments for such diseases include medications that seek to control blood pressure and blood cholesterol e.g. angiotension converting enzyme inhibitors (ACE inhibitors), angiotension receptor blockers (ARBs) or statins. Despite current treatment, there still exists a need for novel therapies to halt progression of chronic kidney disease and/or treat the signs and symptoms of nephritic syndrome.

Patent application WO03/068747 (SmithKline Beecham Corporation) discloses a series of nicotinamide derivatives that are useful as p38 inhibitors. The compound 6-(5-cyclopropylcarbamoyl-3-fluoro-2-methyl-phenyl)-N-(2,2-dimethylpropyl)-nicotinamide is specifically described therein. The statement of non-proprietary name adopted by the USAN Council for this compound is losmapimod.

SUMMARY OF THE INVENTION

In a first aspect there is provided the compound 6-(5-cyclopropylcarbamoyl-3-fluoro-2-methyl-phenyl)-N-(2,2-dimethylpropyl)-nicotinamide or a pharmaceutically acceptable salt thereof for use in the treatment of a glomerular disease.

In a second aspect there is provided a pharmaceutical formulation comprising the compound 6-(5-cyclopropylcarbamoyl-3-fluoro-2-methyl-phenyl)-N-(2,2-dimethylpropyl)-nicotinamide or a pharmaceutically acceptable salt thereof for use in the treatment of a glomerular disease.

In a third aspect there is provided a combination product comprising 6-(5-cyclopropylcarbamoyl-3-fluoro-2-methyl-phenyl)-N-(2,2-dimethylpropyl)-nicotinamide or a pharmaceutically acceptable salt thereof and one or more other therapeutic agents which are suitable for the treatment of a glomerular disease.

In a fourth aspect there is provided a method for treating a glomerular disease in a subject in need thereof which comprises administering to said subject the compound 6-(5-cyclopropylcarbamoyl-3-fluoro-2-methyl-phenyl)-N-(2,2-dimethylpropyl)-nicotinamide or a pharmaceutically acceptable salt thereof.

In a fifth aspect there is provided the use of 6-(5-cyclopropylcarbamoyl-3-fluoro-2-methyl-phenyl)-N-(2,2-dimethylpropyl)-nicotinamide or a pharmaceutically acceptable salt thereof in the manufacture of a medicament for use in the treatment of a glomerular disease.

DETAILED DESCRIPTION OF THE INVENTION

According to the present invention there is provided the compound 6-(5-cyclopropylcarbamoyl-3-fluoro-2-methyl-phenyl)-N-(2,2-dimethylpropyl)-nicotinamide, that is to say, the compound having the formula (I)

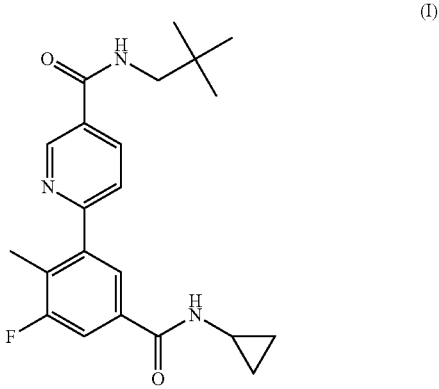 [SMILES: Cc1c(F)cc(C(=O)NC2CC2)cc1-c1ccc(C(=O)NCC(C)(C)C)cn1]

(I)

or a pharmaceutically acceptable salt thereof for use in the treatment of a glomerular disease.

In one embodiment the glomerular disease is glomerulonephritis.

In one embodiment the glomerular disease is glomerulosclerosis.

In a particular embodiment the glomerular disease is focal segmental glomerulosclerosis (FSGS).

In a particular embodiment the glomerular disease is diabetic nephropathy.

In a particular embodiment the glomerular disease is glomerular hypertension.

In a further particular embodiment the glomerular disease is selected from the group consisting of systemic lupus erythematosus (SLE), IgA nephropathy, Goodpasture Syndrome, membrous nephropathy, hereditary renal disease, infection related glomerular disease, chronic pyelonephritis, Alport's Syndrome, periarteritis nodosa nephritis associated with amyloidosis, glomerular disease caused by HIV and toxins.

The compound 6-(5-cyclopropylcarbamoyl-3-fluoro-2-methyl-phenyl)-N-(2,2-dimethylpropyl)-nicotinamide or a pharmaceutically acceptable salt thereof may be prepared according to procedures described in patent application WO03/068747 (as example 36).

Pharmaceutically acceptable salts of the compound 6-(5-cyclopropylcarbamoyl-3-fluoro-2-methyl-phenyl)-N-(2,2-dimethylpropyl)-nicotinamide are non toxic salts and include examples described in patent application WO03/068747, the contents of which is incorporated by reference. For a review of suitable pharmaceutically acceptable salts see also Berge et al., J. Pharm. Sci., 66:1-19, (1977).

In one embodiment the compound 6-(5-cyclopropylcarbamoyl-3-fluoro-2-methyl-phenyl)-N-(2,2-dimethylpropyl)-nicotinamide is in the form of a free base.

Whilst it is possible for the compound 6-(5-cyclopropylcarbamoyl-3-fluoro-2-methyl-phenyl)-N-(2,2-dimethylpropyl)-nicotinamide or a pharmaceutically acceptable salt thereof to be administered as the raw chemical it would typically be administered in the form of a pharmaceutical composition. 6-(5-cyclopropylcarbamoyl-3-fluoro-2-methyl-phenyl)-N-(2,2-dimethylpropyl)-nicotinamide or a pharmaceutically acceptable salt may therefore be formulated for administration in any suitable manner that is known to those skilled in the art. It may, for example, be formulated for topical administration, transdermal administration, administration by inhalation, oral administration or parenteral administration (e.g. intravenously, intravascularly or subcutaneously). Suitable methods for formulating 6-(5-cyclopropylcarbamoyl-3-fluoro-2-methyl-phenyl)-N-(2,2-dimethylpropyl)-nicotinamide or a pharmaceutically acceptable salt include those described in patent application WO03/068747 and/or the methods that are familiar to those skilled in the art, which are described in Remington: The Science and Practice of Pharmacy, 21$^{st}$ Edition 2006.

In a further aspect there is provided a pharmaceutical formulation comprising the compound 6-(5-cyclopropylcarbamoyl-3-fluoro-2-methyl-phenyl)-N-(2,2-dimethylpropyl)-nicotinamide or a pharmaceutically acceptable salt thereof for use in the treatment of a glomerular disease.

In one embodiment there is provided a pharmaceutical formulation comprising the compound 6-(5-cyclopropylcarbamoyl-3-fluoro-2-methyl-phenyl)-N-(2,2-dimethylpropyl)-nicotinamide or a pharmaceutically acceptable salt thereof for use in the treatment of focal segmental glomerulosclerosis (FSGS).

In one embodiment the pharmaceutical formulation is adapted for oral administration.

In a particular embodiment 6-(5-cyclopropylcarbamoyl-3-fluoro-2-methyl-phenyl)-N-(2,2-dimethylpropyl)-nicotinamide or a pharmaceutically acceptable salt thereof is administered orally with a dosage in the range 1 mg twice per day (bid) to 30 mg twice per day (bid), particularly 2.5 mg twice per day (bid) to 15 mg twice per day (bid), even more particularly 7.5 mg twice per day (bid) or 15 mg twice per day (bid).

The present invention also provides for a method for treating a glomerular disease in a subject in need thereof which comprises administering the compound 6-(5-cyclopropylcarbamoyl-3-fluoro-2-methyl-phenyl)-N-(2,2-dimethylpropyl)-nicotinamide or a pharmaceutically acceptable salt.

Suitably the subject in need thereof is a mammal, particularly a human.

In one embodiment there is provided a method for treating a glomerular disease in a subject in need thereof which comprises administering to said subject a therapeutically effective amount of the compound 6-(5-cyclopropylcarbamoyl-3-fluoro-2-methyl-phenyl)-N-(2,2-dimethylpropyl)-nicotinamide or a pharmaceutically acceptable salt thereof.

In a particular embodiment there is provided a method for treating focal segmental glomerulosclerosis (FSGS) in a subject in need thereof which comprises administering to said subject a therapeutically effective amount of the compound 6-(5-cyclopropylcarbamoyl-3-fluoro-2-methyl-phenyl)-N-(2,2-dimethylpropyl)-nicotinamide or a pharmaceutically acceptable salt thereof.

As used herein, the term "therapeutically effective amount" means that amount of a 6-(5-cyclopropylcarbamoyl-3-fluoro-2-methyl-phenyl)-N-(2,2-dimethylpropyl)-nicotinamide that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

Also provided is the use of 6-(5-cyclopropylcarbamoyl-3-fluoro-2-methyl-phenyl)-N-(2,2-dimethylpropyl)-nicotinamide or a pharmaceutically acceptable salt thereof in the manufacture of a medicament for use in the treatment of a glomerular disease. In a particular embodiment there is provided the use of 6-(5-cyclopropylcarbamoyl-3-fluoro-2-methyl-phenyl)-N-(2,2-dimethylpropyl)-nicotinamide or a pharmaceutically acceptable salt thereof in the manufacture of a medicament for use in the treatment of focal segmental glomerulosclerosis (FSGS). It will be appreciated that 6-(5-cyclopropylcarbamoyl-3-fluoro-2-methyl-phenyl)-N-(2,2-dimethylpropyl)-nicotinamide or a pharmaceutically acceptable salt thereof may be employed alone or in combination with other therapeutic agents which are suitable for the treatment of a glomerular disease.

Therefore, the present invention further provides a combination product comprising 6-(5-cyclopropylcarbamoyl-3-fluoro-2-methyl-phenyl)-N-(2,2-dimethylpropyl)-nicotinamide or a pharmaceutically acceptable salt thereof and one or more other therapeutic agents which are suitable for the treatment of a glomerular disease.

In a particular embodiment there is provided a combination product comprising 6-(5-cyclopropylcarbamoyl-3-fluoro-2-methyl-phenyl)-N-(2,2-dimethylpropyl)-nicotinamide or a pharmaceutically acceptable salt thereof and one or more other therapeutic agents which are suitable for the treatment of focal segmental glomerulosclerosis (FSGS).

6-(5-Cyclopropylcarbamoyl-3-fluoro-2-methyl-phenyl)-N-(2,2-dimethylpropyl)-nicotinamide and the other therapeutically active agent(s) may be administered together or separately and, when administered separately, this may occur simultaneously or sequentially in any order. The amounts of 6-(5-cyclopropylcarbamoyl-3-fluoro-2-methyl-phenyl)-N-(2,2-dimethylpropyl)-nicotinamide or a pharmaceutically acceptable salt thereof and the other pharmaceutically active agent(s) and the relative timings of administration will be selected in order to achieve the desired combined therapeutic effect.

It will be clear to a person skilled in the art that, where appropriate, the other therapeutic ingredient(s) may be used in the form of salts, (e.g. as alkali metal or amine salts or as acid addition salts), or prodrugs, or as esters (e.g. lower alkyl esters), or as solvates (e.g. hydrates) to optimise the activity and/or stability and/or physical characteristics (e.g. solubility) of the therapeutic ingredient. It will be clear also that where appropriate, the therapeutic ingredients may be used in optically pure form.

In one embodiment there is provided a combination product comprising 6-(5-cyclopropylcarbamoyl-3-fluoro-2-methyl-phenyl)-N-(2,2-dimethylpropyl)-nicotinamide, or a pharmaceutically acceptable salt thereof, together with an ACE inhibitor, ARB or a statin.

In a further embodiment there is provided a combination product comprising 6-(5-cyclopropylcarbamoyl-3-fluoro-2-methyl-phenyl)-N-(2,2-dimethylpropyl)-nicotinamide, or a pharmaceutically acceptable salt thereof, together with a corticosteroid or a calcinerun inhibitor (e.g. tacrolimus).

The following example illustrates the invention.

Example 1

A Pharmaceutical Formulation of 6-(5-cyclopropyl-carbamoyl-3-fluoro-2-methyl-phenyl)-N-(2,2-dimethylpropyl)-nicotinamide (losmapimod) Suitable for Oral Administration A representative formulation for use in this invention is shown in the table below.

| Component | mg/tablet | % w/w |
| --- | --- | --- |
| Intragranular | | |
| 6-(5-cyclopropylcarbamoyl-3-fluoro-2-methyl-phenyl)-N-(2,2-dimethylpropyl)-nicotinamide (micronized) | 7.5 | 5.0 |
| Lactose Monohydrate | 67.9 | 45.3 |
| Microcrystalline Cellulose | 30.0 | 20.0 |
| Sodium Starch Glycolate | 4.5 | 3.0 |
| Povidone | 4.5 | 3.0 |
| Extragranular | | |
| Microcrystalline Cellulose | 30.0 | 20.0 |
| Sodium Starch Glycolate | 4.5 | 3.0 |
| Magnesium Stearate | 1.125 | 0.75 |
| Core Compression Weight | 150 mg | |
| Film Coat | | |
| Opadry White OY-S-28876 | 4.5 | 3.0 |

Example 2

An Efficacy, Safety and Tolerability Study Relating to Losmapimod in the Treatment of Primary (Idiopathic) Focal Segmental Glomerulosclerosis (FSGS)

This evaluation may be carried out by treatment of FSGS patients having nephrotic range proteinuria (urinary protein/creatinine [Up/c] ratio>3) and a history of steroid resistance, including relapse of proteinuria after steroid treatment (n=approximately 20). Losmapimod is orally administered twice daily over a 24-week treatment phase (7.5 mg BID for 2 weeks followed by 15 mg BID for 22 weeks). The primary efficacy endpoint of proteinuria is evaluated by the measurement of the Up/c ratio, assessed from a first morning urine sample, with a responder being a patient with a 50% proteinuria reduction from baseline at the end of treatment. Safety and tolerability is monitored by clinical laboratory evaluations (including liver function tests and serum creatinine), vital signs, ECGs, and adverse events.

All publications, including but not limited to patents and patent applications, cited in this specification are herein incorporated by reference as if each individual publication were specifically and individually indicated to be incorporated by reference herein as though fully set forth.

The invention claimed is:

1. A method for treating focal segmental glomerulosclerosis (FSGS) in a subject in need thereof comprising administering to said subject a pharmaceutical formulation comprising the compound 6-(5-cyclopropylcarbamoyl-3-fluoro-2-methyl-phenyl)-N-(2,2-dimethylpropyl)-nicotinamide or a pharmaceutically acceptable salt thereof.

2. The method of claim 1, wherein the pharmaceutical formulation is adapted for oral administration.

3. The method of claim 1, wherein the pharmaceutical formulation comprises one or more other therapeutic agents which are suitable for the treatment of focal segmental glomerulosclerosis (FSGS).

4. The method of claim 1, wherein the compound 6-(5-cyclopropylcarbamoyl-3-fluoro-2-methyl-phenyl)-N-(2,2-dimethylpropyl)-nicotinamide is in the form of a free base.

5. The method of claim 4, wherein the pharmaceutical formulation is adapted for oral administration.

6. The method of claim 4, wherein the pharmaceutical formulation further comprises one or more other therapeutic agents which are suitable for the treatment of focal segmental glomerulosclerosis (FSGS).

* * * * *